United States Patent [19]
Braxton et al.

[11] Patent Number: 5,654,146
[45] Date of Patent: Aug. 5, 1997

[54] HUMAN ICE HOMOLOG

[75] Inventors: Scott Michael Braxton, San Mateo; Angelo M. Delegeane, Hayward; Dinh Diep, San Francisco, all of Calif.

[73] Assignee: Incyte Pharmaceuticals, Inc., Palo Alto, Calif.

[21] Appl. No.: 443,865

[22] Filed: May 31, 1995

[51] Int. Cl.$^6$ .............. C12N 9/00; C12N 15/12; C12Q 1/68; G01N 33/573
[52] U.S. Cl. .............. 435/6; 435/7.4; 435/69.2; 435/183; 435/320.1; 435/358; 536/23.2
[58] Field of Search .................. 536/23.2, 24.5; 435/6, 320.1, 240.2, 69.2, 7.1, 7.4; 424/172.1; 530/350, 387.1

[56] References Cited

FOREIGN PATENT DOCUMENTS

WO 95/27792  10/1995  WIPO.
WO 96/04387  2/1996  WIPO.

OTHER PUBLICATIONS

Ayala et al, "IL-1 β–Converting Enzyme Is Present in Monocytic Cells as an Inactive 45–kDa Precursor," J Immunol 53:2592–2599 (1994).
Abbas et al, "Effector Mechanisms of Immune Responses," Cellular and Molecular Immunology, Chapter 12, pp. 240–260, W.B. Saunders Company (1994).
Li et al., "Mice Deficient in IL–1β–Converting Enzyme are Defective in Production of Mature IL–1β and Resistant to Endotoxic Shock," Cell 80:401–411 (1995).
Howard et al., "IL–1–Converting Enzyme Requires Aspartic Acid Residues for Processing of the IL–β Precursor at Two Distinct Sites and does not Cleave 31–kDa IL–1α," J. Immunol 147:2964–2969 (1991).
Carruth et al., "Involvement of a Calpain–like Protease in the Processing of the Murine Interleukin 1αPrecursor," J Biol Chem 266:12162–12167 (1991).

Miura et al., "Induction of Apoptosis in Fibroblasts by IL–1β–Converting Enzyme, a Mammalian Homolog of the C. Elegans Cell Death Gene ced–e, " Cell 75:653–660 (1993).
Walker et al., "Crystal Structure of the Cysterine Protease Interleukin–1β–Converting Engyme: A (p20/p10)$_2$ Homodimer, " Cell 78:343–352 (1994).
Yuan et al., "The C. Elegans Cell Death Gene ced–3 Encodes a Protein Similar to Mammalian Interleukin–1β–Converting Enzyme," Cell 75:641–652 (1993).
Dinarello et al., "The Role of Interleukin–1 in Disease," N Engl J Med 328:106–13 (1993).
Tsuchiya et al., "Establishment and Characterization of a Human Acute Monocytic Leukemia Cell Line (THP–1), " Int J Cancer 26:171–176 (1980).
Auwerx, "The human leukemia cell line, THP–1: A multi-facetted model for the study of monocyte–macrophage differentiation," Experientia 47:22–31 (1991).
Cochran et al., "Regulation of interleukin–1β and tumor necrosis factor secretion by the human monocytic leukemia cell line, THP–1, " Agents and Actions 27:271–273 (1989).

(List continued on next page.)

*Primary Examiner*—George C. Elliott
*Assistant Examiner*—Amy J. Nelson
*Attorney, Agent, or Firm*—Barbara J. Luther; Lucy J. Billings; Incyte Pharmaceuticals, Inc.

[57] ABSTRACT

The present invention provides nucleotide and amino acid sequences that identify and encode a new human interleukin-1 converting enzyme homolog (ICEY). The present invention also provides for expression vectors for the production of purified ICEY, hybridization probes for the detection of ICEY-encoding nucleotide sequences, genetically engineered host cells for the expression of ICEY, diagnostic tests for ICEY or for polynucleotides encoding ICEY, and use of the protein to produce antibodies capable of binding specifically to the protein and use of the protein to screen for inhibitors.

10 Claims, 7 Drawing Sheets

```
                      9              18             27              36             45              54
5'  TGC ATT CGG ACG AGG TTA GCT ATG GCT GAA GAC AAC CAC AAA AAA AAA ACA GTT
     C   I   R   T   R   L   A   M   A   E   D   N   H   K   K   K   T   V 63             72             81              90             99             108
    AAG ATG TTG GAA TAC CTG GGC AAA GAT GTT CTT CAT GGT GTT TTT AAT TAT TTG
     K   M   L   E   Y   L   G   K   D   V   L   H   G   V   F   N   Y   L 117            126            135             144            153             162
    GCA AAA CAC GAT GTT CTG ACA TTG AAG GAA GAG AAG AAA AAA TAT TAT GAT
     A   K   H   D   V   L   T   L   K   E   E   E   K   K   K   Y   Y   D 171            180            189             198            207             216
    ACC AAA ATT GAA GAC AAG GCC CTG ATC TTG GTA GAC TCT TTG GAA AGA ATC GCG
     T   K   I   E   D   K   A   L   I   L   V   D   S   L   E   R   I   A 225            234            243             252            261             270
    TGG TCA TCA AAT GTT TAC CCA AAC ACT TCT CAA TAT GGA CCA AAA GAT CAC CAG
     W   S   S   N   V   Y   P   N   T   S   Q   Y   G   P   K   D   H   Q 279            288            297             306            315             324
    TGT AAA ACC TCT TCT GCA AAT CGA GGT GGA CCA CCT GAG TCA GCA GAA TCT ACA
     C   K   T   S   S   A   N   R   G   G   P   P   E   S   A   E   S   T 333            342            351             360            369             378
    AAT ATA CTC AAA CTT TGT CCT CGT GAA GAA TTC CTG AGA CTG TGT AAA AAA AAT
     N   I   L   K   L   C   P   R   E   E   F   L   R   L   C   K   K   N 387            396            405             414            423             432
    CAT GAT GAG ATC TAT CCA ATA AAA AAG AGA GAC CGC AGA CGC CTG GCT CTC
     H   D   E   I   Y   P   I   K   K   R   E   D   R   R   R   L   A   L
```

OTHER PUBLICATIONS

Cerretti et al., "Molecular Cloning of the Interleukin-1beta Converting Enzyme", Science, vol. 226, pp. 97–100. Apr. 3, 1992.

Miller et al., "Purification and Characterization of Active Human Interleukin-1beta-Converting Enzyme from THP.1 Monocytic Cells", The Journal of Biological Chemistry, vol. 268, No. 24, pp. 18062–18069. Aug. 25, 1993.

Miura et al., "Induction of Apoptosis in Fibroblasts by IL-1beta-Converting Enzyme, a Mammalian Homolog of the C. elegans Cell Death Gene ced-3", Cell, vol. 75, pp. 653–660. Nov. 19, 1993.

Munday et al., "Molecular cloning and pro-apoptotic activity of ICErelII and ICErelIII, . . . " *J. Of Biological Chemistry,* 270(26):15870–15876 (1995).

Faucheu et al., "A novel protease similar to the interleukin-1-beta converting enzyme induces apoptosis in transfected cells," *Embo Journal,* 14(9):1914–1922.

FIG. 1A

```
5' TGC ATT CGG ACG AGG TTA GCT ATG GAA GAC AAC CAC AAA AAA ACA GTT
    C   I   R   T   R   L   A   M   E   D   N   H   K   K   T   V
                9          18          27          36          45      54

AAG ATG TTG GAA TAC CTG GGC AAA GAT GTT CTT CAT GGT GTT TTT AAT TAT TTG
    K   M   L   E   Y   L   G   K   D   V   L   H   G   V   F   N   Y   L
               63          72          81          90          99         108

GCA AAA CAC GAT GTT CTG ACA TTG AAG GAA GAG AAG AAA TAT TAT GAT
    A   K   H   D   V   L   T   L   K   E   E   K   K   Y   Y   D
              117         126         135         144         153     162

ACC AAA ATT GAA GAC AAG GCC CTG AAT CGA ATC TTG GTA GAC TCT TTG GAA AGA ATC GCG
    T   K   I   E   D   K   A   L   N   R   I   L   V   D   S   L   E   R   I   A
              171         180         189         198         207         216

TGG TCA AAT GTT TAC CCA AAT CGA ATC TCT CAA ACT TCT TTG GAA TCA CCA AAA CAG
    W   S   N   V   Y   P   N   R   I   S   Q   T   S   L   E   S   P   K   Q
              225         234         243         252         261     270

TGT AAA GAC TCT TCT GCA AAT CGA ATC GGT GGA CCA CCT GAG TCA AGA CTG GCA GAA TCT ACA
    C   K   D   S   S   A   N   R   I   G   G   P   P   E   S   R   L   A   E   S   T
              279         288         297         306         315         324

AAT ATA CTC AAA CTT TGT CCT CGT GAA TTC CTG AGA GAC CGC AGA AAA AAT
    N   I   L   K   L   C   P   R   E   F   L   R   D   R   R   K   N
              333         342         351         360         369     378

CAT GAT GAG ATC TAT ATC CCA ATA AAA AGA AAG AGA GAG GAC CGC CTG GCT CTC
    H   D   E   I   Y   I   P   I   K   R   K   R   E   D   R   L   A   L
              387         396         405         414         423     432
```

FIG. 1B

```
      ATC  441  ATA  AAT  ACA  450  TTT  GAT  CAC  459  CCT  GCA  AGG  468  GGG  GCT  CAC  477      486
      ATA  TGC  ATA  AAT  ACA  AAG  TTT  GAT  CAC  CTG  CCT  GCA  AGG  AAT  GGG  GCT  CAC  TAT
       I    C    I    N    T    K    F    D    H    L    P    A    R    N    G    A    H    Y

GAC  495  ATC  GGG  ATG  504  AGG  CTG  CAA  513  CTT  GGC  TAC  522  CTG  ACT  GTG  531  GTT  540
      GAC  ATC  ATC  GGG  ATG  AAA  AGG  CTG  CAA  CTT  CTT  GGC  TAC  GTG  CTG  ACT  GTG  GCC
       D    I    I    G    M    K    R    L    Q    L    L    G    Y    V    L    T    V    A

GAA  549  CTC  ACA  GCC  558  AGG  GAT  ATG  567  GAG  TCA  GTG  576  CTG  AGG  TTT  585  GCA  594
      AAT  CTC  ACA  GCC  AGG  GAT  ATG  GAG  TCA  GTG  CTG  AGG  GCA  TTT  GCT  GCC
       N    L    T    A    R    D    M    E    S    V    L    R    A    F    A    A

AGA  603  CAC  AAG  612  TCC  GAT  621  AGC  ACG  TTC  630  TTG  GTA  CTC  639  ATG  TCT  CAT  648
      GAG  CAC  AAG  TCC  GAT  AGC  ACG  TTC  TTG  GTA  CTC  ATG  TCT  CAT  GGC
       E    H    K    S    D    S    T    F    L    V    L    M    S    H    G

ATC  657  GGA  TGC  666  ATC  CCT  675  GCG  CAT  AAA  684  AAG  AAA  CAT  693  CCG  GAT  GTG  702  CTG
      GAG  GGA  TGC  ATC  CCT  GCG  CAT  AAA  AAG  AAA  CAT  CCG  GAT  GTG  CTG
       E    G    C    I    P    A    H    K    K    K    H    P    D    V    L

CTT  711  ACC  ATC  720  TTC  CAG  ATA  729  TTC  AAC  AAC  738  CGC  AAC  TGC  747  CTC  AGT  CTA  756  AAG
      TAT  ACC  ATC  TTC  CAG  ATA  TTC  AAC  AAC  CGC  AAC  TGC  CTC  AGT  CTA  AAG
       Y    T    I    F    Q    I    F    N    N    R    N    C    L    S    L    K

GAC  765  AAG  GTC  774  ATT  GTC  783  CAG  GCC  TGC  792  AGA  GGT  GAA  801  AAA  CAT  GGG  810  AAC
      AAA  AAG  GTC  ATT  GTC  CAG  GCC  TGC  AGA  GGT  GAA  AAA  CAT  GGG  AAC
       K    K    V    I    V    Q    A    C    R    G    E    K    H    G    N

TCT  819  AGA  CTC  828  TCC  ACA  CCT  837  TGC  ATC  ACT  846  CTT  CAC  AGT  855  CAT  CTG  AGA  864  ACC
      GGT  AGA  CTC  TCC  ACA  CCT  TGC  ATC  ACT  CTT  CAC  AGT  CAT  CTG  AGA  ACC
       G    R    L    S    T    P    C    I    T    L    H    S    H    L    R    T
```

```
TGG AGG CAG ATT CTG TTT TCA AGA CCC CGA GGA GAA GGA CTT CAT TGC TGT TCT
 W   R   Q   I   L   F   S   R   P   R   G   E   G   L   H   C   C   S
873         882         891         900         909         918

GTT CTT CAA CAC CAC ATA ACG TGT CCT GGA GAG ACC GCA CAA GGG GCT CCA TCT
 V   L   Q   H   H   I   T   C   P   G   E   T   A   Q   G   A   P   S
927         936         945         954         963         972

TCA TTA CGG AAC TCA TCA CAT GCT TCC AGA ATT CTT TCT CTC CAC CTA ATG
 S   L   R   N   S   S   H   A   S   R   I   L   S   L   H   L   M
981         990         999        1008        1017        1026

GAA ATA TTT CGG GAG GTA CAG AAA TCA TTT GAA GTT CCA CAG GCT AAA GCC CAG
 E   I   F   R   E   V   Q   K   S   F   E   V   P   Q   A   K   A   Q
1035        1044        1053        1062        1071        1080

ATG CCC ACC ATA GAA CGA GCA ACC TTG ACA AGA GAT TTC TAC CTC TTT CCT GGC
 M   P   T   I   E   R   A   T   L   T   R   D   F   Y   L   F   P   G
1089        1098        1107        1116        1125        1134

AAT TGA AAA TGA AAC CAC AGG CAG CCC AGC CCT CTG TCA ACA TCA AAG AGC
 N   *
1143        1152        1161        1170        1179        1188

ACA TTT ACC AGT ATA GCT TGC ATA GTC AAT ATT TGG TAT TTC AAT AAA AGT AAA
1197        1206        1215        1224        1233

GAC TGT ATC TTT TTA AAA AAA AAA AAA AAA AA 3'
1251        1260        1269
```

FIG. 1C

```
     M A D D V L K E K T V L F L E S L G E G V L N G V L D E L X        MAJORITY
                   10              20              30
  1  M A E D N H K K K T V K M L E Y L G K D V L H G V F N Y L X        NEW 1.->14775.COR2
  1  M A D K V L K E K R K L F I R S M G E G T I N G L L D E L L        NEW U13697.AA.TXT

Q T D V L T L E E E K V K R E D A T V E D K A L A L V D S          MAJORITY
                   40              50              60
 31  K H D V L T L K E E E K K K Y Y D T K I E D K A L I L V D S        NEW 1.->14775.COR2
 31  Q T R V L N K E E M E K V K R E N A T V M D K T R A L I D S        NEW U13697.AA.TXT

V E R I A K G A N A Y Q I T I T Y G C E D D S Y L A G S A G        MAJORITY
                   70              80              90
 61  L E R I A W S S N V Y P N T S Q Y G P K D H Q C K T S S A N        NEW 1.->14775.COR2
 61  V - - I P K G A Q A C Q I C I T Y I C E E D S Y L A G T L G        NEW U13697.AA.TXT

L G G A P E A A E S T N A L P T S S G S E G N V K L C S L E        MAJORITY
                  100             110             120
 91  R G G P P E S A E S T N I L - - - - - - - - - - K L C P R E        NEW 1.->14775.COR2
 89  L S A A P Q A V Q D N P A M P T S S G S E G N V K L C S L E        NEW U13697.AA.TXT

E A L R L W K Q N S A E I Y P I K D K S S R T R L A L I I C        MAJORITY
                  130             140             150
111  E F L R L C K K N H D E I Y P I K K R E D R R R L A L I I C        NEW 1.->14775.COR2
119  E A Q R I W K Q K S A E I Y P I M D K S S R T R L A L I I C        NEW U13697.AA.TXT

N T E F D S L P A R T G A E V D I V G M T R L L Q G L G Y S        MAJORITY
                  160             170             180
141  N T K F D H L P A R N G A H Y D I V G M K R L L Q G L G Y T        NEW 1.->14775.COR2
149  N E E F D S I P R R T G A E V D I T G M T M L L Q N L G Y S        NEW U13697.AA.TXT

V V A E K N L T A S D M T S V L E A F A A R P E H K S S D S        MAJORITY
                  190             200             210
171  V V A E K N L T A R D M E S V L R A F A A R P E H K S S D S        NEW 1.->14775.COR2
179  V D V K K N L T A S D M T T E L E A F A H R P E H K T S D S        NEW U13697.AA.TXT

T F L V L M S H G I L E G I C G K A H S E Q V P D V L L D          MAJORITY
                  220             230             240
201  T F L V L M S H G I L E G I C G P A H K K K K P D V L L Y D        NEW 1.->14775.COR2
209  T F L V F M S H G I R E G I C G K K H S E Q V P D I L Q L N        NEW U13697.AA.TXT
```

FIG. 2A

```
         A I F N I L N T K N C L S L K D K P K V I I V Q A C R G D S    MAJORITY
                    250             260               270
    231  T I F Q I F N N R N C L S L K D K P K V I I V Q A C R G E K    NEW 1 -->14775.COR2
    239  A I F N M L N T K N C P S L K D K P K V I I I Q A C R G D S    NEW U13697.AA.TXT

H G V V W F G D S V G V S G I L S L Q S S E E L E A D A V K    MAJORITY
                    280             290               300
    261  H G N S - - G Q R L S T P C I I S S Q S S E N L E A D S V F    NEW 1 -->14775.COR2
    269  P G V V W F K D S V G V S G N L S L P T T E F E D D A I K      NEW U13697.AA.TXT

K A H I E K T S L A F C S S T P D N V S W R D R T R G S V F    MAJORITY
                    310             320               330
    289  K T P R R R T S L L F C S S T P H N V S W R D R T R G S I F    NEW 1 -->14775.COR2
    299  K A H I E K D F I A F C S S T P D N V S W R H P T M G S V F    NEW U13697.AA.TXT

I G E L I E H L Q E I A F S C D V G E I F S E V Q K S F E V    MAJORITY
                    340             350               360
    319  I G E L M H M L P E I F F S P P N G N I - S E V Q K S F E V    NEW 1 -->14775.COR2
    329  I G R L I E H M Q E Y A C S C D V E E I F R K V R F S F E Q    NEW U13697.AA.TXT

P D G K A Q M P T I E R A T L T R D F Y L F P G N              MAJORITY
                    370             380
    348  P Q A K A Q M P T I E R A T L T R D F Y L F P G N              NEW 1 -->14775.COR2
    359  P D G R A Q M P T T E R V T L T R C F Y L F P G H              NEW U13697.AA.TXT
```

FIG. 2B

SEQUENCE LISTING ( 1 ) GENERAL INFORMATION:

( i i i ) NUMBER OF SEQUENCES:6

( 2 ) INFORMATION FOR SEQ ID NO:1:

( i ) SEQUENCE CHARACTERISTICS:
        ( A ) LENGTH: 303 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP-1
        ( B ) CLONE: 014775

( x i ) SEQUENCE DESCRIPTION: SEQ ID NO:1:

| | | | | | |
|---|---|---|---|---|---|
| ACAGTCTTTA | CTTTATTGA | AATACCAAAT | ATTGACTATG | CAAGCTATAC | TGGTAAATGT | 60 |
| CTCTTTGATG | TTGACAGAGG | AGGGCTGGGC | TGCCTGTGGT | TTCATTTTCA | ATTGCCAGGA | 120 |
| AAGAGGTAGA | AATCTCTTGT | CAAGGTTGCT | CGTTCTATGG | TGGGCATCTG | GGCTTTAGCC | 180 |
| TGTGGAACTT | CAAATGATTT | CTGTACCTTC | CGAAATATTT | CCATTAGGTG | GCAGCAGCAA | 240 |
| GAATATTTCT | GGAAGCATGT | GATGAGTTCC | GTAATGAGAT | GGAGCCCCTT | TGCGGTCTCT | 300 |
| TTC | | | | | | 303 |

( 2 ) INFORMATION FOR SEQ ID NO:2:

( i ) SEQUENCE CHARACTERISTICS:
        ( A ) LENGTH: 167 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( E ) HAPLOTYPE: THP-1

( v i i ) IMMEDIATE SOURCE:
        ( A ) LIBRARY: 157811

( x i ) SEQUENCE DESCRIPTION: SEQ ID NO:2:

| | | | | | |
|---|---|---|---|---|---|
| CAAACACTTC | TCAATATGGA | CCAAAAGATC | ACCAGTGTAA | AACCTCTTCT | GCAAATCGAG | 60 |
| GCTGGCCACC | TGCAGCAGAT | CTCAAATATA | CTCAAACTTT | GTCCTCGTGA | AGAATTCCTG | 120 |
| AGACTGTGTA | AAAAAAATCA | TGATGAGATC | TATCCAATAA | AAAAGAG | | 167 |

( 2 ) INFORMATION FOR SEQ ID NO:3:

( i ) SEQUENCE CHARACTERISTICS:

(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

CCCCCAGGTT CTCAGATGAC TGT 23

(2) INFORMATION FOR SEQ ID NO:4:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

ACAGTCATCT GAGAACCTGG GGG 23

(2) INFORMATION FOR SEQ ID NO:5:

(i) SEQUENCE CHARACTERISTICS:
(A) LENGTH: 1274 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(A) LIBRARY: THP-1
(B) CLONE: 14775

(xi) SEQUENCE DESCRIPTION: SEQ ID NO:5:

| | | | | | |
|---|---|---|---|---|---|
| TGCATTCGGA | CGAGGTTAGC | TATGGCTGAA | GACAACCACA | AAAAAAAAAC | AGTTAAGATG | 60
| TTGGAATACC | TGGGCAAAGA | TGTTCTTCAT | GGTGTTTTTA | ATTATTTGGC | AAAACACGAT | 120
| GTTCTGACAT | TGAAGGAAGA | GGAAAAGAAA | AAATATTATG | ATACCAAAAT | TGAAGACAAG | 180
| GCCCTGATCT | TGGTAGACTC | TTTGGAAAGA | ATCGCGTGGT | CATCAAATGT | TTACCCAAAC | 240
| ACTTCTCAAT | ATGGACCAAA | AGATCACCAG | TGTAAAACCT | CTTCTGCAAA | TCGAGGTGGA | 300
| CCACCTGAGT | CAGCAGAATC | TACAAATATA | CTCAAACTTT | GTCCTCGTGA | AGAATTCCTG | 360
| AGACTGTGTA | AAAAAAATCA | TGATGAGATC | TATCCAATAA | AAAGAGAGA | GGACCGCAGA | 420
| CGCCTGGCTC | TCATCATATG | CAATACAAAG | TTTGATCACC | TGCCTGCAAG | GAATGGGGCT | 480
| CACTATGACA | TCGTGGGGAT | GAAAAGGCTG | CTTCAAGGCC | TGGGCTACAC | TGTGGTTGCC | 540
| GAAAAGAATC | TCACAGCCAG | GGATATGGAG | TCAGTGCTGA | GGGCATTTGC | TGCCAGACCA | 600
| GAGCACAAGT | CCTCTGACAG | CACGTTCTTG | GTACTCATGT | CTCATGGCAT | CCTAGAGGGA | 660
| ATCTGCGGAC | CTGCGCATAA | AAAGAAAAAA | CCGGATGTGC | TGCTTTATGA | CACCATCTTC | 720
| CAGATATTCA | ACAACCGCAA | CTGCCTCAGT | CTAAAGGACA | AACCCAAGGT | CATCATTGTC | 780
| CAGGCCTGCA | GAGGTGAAAA | ACATGGGAAC | TCTGGTCAGA | GACTCTCCAC | ACCTTGCATC | 840
| ATCTCTTCAC | AGTCATCTGA | GAACCTGGAG | GCAGATTCTG | TTTTCAAGAC | CCCGAGGAGA | 900
| AGGACTTCAT | TGCTGTTCTG | TTCTTCAACA | CCACATAACG | TGTCCTGGAG | AGACCGCACA | 960
| AGGGGCTCCA | TCTTCATTGG | GGAACTCATG | CACATGCTTC | CAGAAATATT | CTTCTCTCCA | 1020
| CCTAATGGAA | ATATTTCGGA | GGTACAGAAA | TCATTTGAAG | TTCCACAGGC | TAAAGCCCAG | 1080
| ATGCCCACCA | TAGAACGAGC | AACCTTGACA | AGAGATTTCT | ACCTCTTTCC | TGGCAATTGA | 1140

```
AAATGAAACC ACAGGCAGCC CAGCCCTCCT CTGTCAACAT CAAAGAGCAC ATTTACCAGT      1200

ATAGCTTGCA TAGTCAATAT TTGGTATTTC AATAAAGTA AAGACTGTAT CTTTTAAAA        1260

AAAAAAAAAA AAAA                                                         1274
```

( 2 ) INFORMATION FOR SEQ ID NO:6:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ala  Glu  Asp  Asn  His  Lys  Lys  Lys  Thr  Val  Lys  Met  Leu  Glu  Tyr
 1                   5                    10                       15

Leu  Gly  Lys  Asp  Val  Leu  His  Gly  Val  Phe  Asn  Tyr  Leu  Ala  Lys  His
              20                    25                        30

Asp  Val  Leu  Thr  Leu  Lys  Glu  Glu  Lys  Lys  Lys  Tyr  Tyr  Asp  Thr
         35                   40                        45

Lys  Ile  Glu  Asp  Lys  Ala  Leu  Ile  Leu  Val  Asp  Ser  Leu  Glu  Arg  Ile
 50                       55                       60

Ala  Trp  Ser  Ser  Asn  Val  Tyr  Pro  Asn  Thr  Ser  Gln  Tyr  Gly  Pro  Lys
 65                  70                       75                       80

Asp  His  Gln  Cys  Lys  Thr  Ser  Ser  Ala  Asn  Arg  Gly  Gly  Pro  Pro  Glu
                  85                       90                       95

Ser  Ala  Glu  Ser  Thr  Asn  Ile  Leu  Lys  Leu  Cys  Pro  Arg  Glu  Phe
                100                    105                    110

Leu  Arg  Leu  Cys  Lys  Lys  Asn  His  Asp  Glu  Ile  Tyr  Pro  Ile  Lys  Lys
              115                    120                    125

Arg  Glu  Asp  Arg  Arg  Arg  Leu  Ala  Leu  Ile  Ile  Cys  Asn  Thr  Lys  Phe
         130                   135                    140

Asp  His  Leu  Pro  Ala  Arg  Asn  Gly  Ala  His  Tyr  Asp  Ile  Val  Gly  Met
145                       150                   155                      160

Lys  Arg  Leu  Leu  Gln  Gly  Leu  Gly  Tyr  Thr  Val  Val  Ala  Glu  Lys  Asn
                   165                   170                      175

Leu  Thr  Ala  Arg  Asp  Met  Glu  Ser  Val  Leu  Arg  Ala  Phe  Ala  Ala  Arg
              180                   185                       190

Pro  Glu  His  Lys  Ser  Ser  Asp  Ser  Thr  Phe  Leu  Val  Leu  Met  Ser  His
         195                    200                      205

Gly  Ile  Leu  Glu  Gly  Ile  Cys  Gly  Pro  Ala  His  Lys  Lys  Lys  Lys  Pro
     210                    215                       220

Asp  Val  Leu  Leu  Tyr  Asp  Thr  Ile  Phe  Gln  Ile  Phe  Asn  Asn  Arg  Asn
225                      230                       235                  240

Cys  Leu  Ser  Leu  Lys  Asp  Lys  Pro  Lys  Val  Ile  Ile  Val  Gln  Ala  Cys
                  245                    250                       255

Arg  Gly  Glu  Lys  His  Gly  Asn  Ser  Gly  Gln  Arg  Leu  Ser  Thr  Pro  Cys
                  260                       265                    270

Ile  Ile  Ser  Ser  Gln  Ser  Ser  Glu  Asn  Leu  Glu  Ala  Asp  Ser  Val  Phe
              275                    280                    285

Lys  Thr  Pro  Arg  Arg  Arg  Thr  Ser  Leu  Leu  Phe  Cys  Ser  Ser  Thr  Pro
         290                    295                    300

His  Asn  Val  Ser  Trp  Arg  Asp  Arg  Thr  Arg  Gly  Ser  Ile  Phe  Ile  Gly
305                       310                   315                     320

Glu  Leu  Met  His  Met  Leu  Pro  Glu  Ile  Phe  Phe  Ser  Pro  Pro  Asn  Gly
```

-continued

```
                     325                       330                         335

Asn  Ile  Ser  Glu  Val  Gln  Lys  Ser  Phe  Glu  Val  Pro  Gln  Ala  Lys  Ala
               340                      345                     350

Gln  Met  Pro  Thr  Ile  Glu  Arg  Ala  Thr  Leu  Thr  Arg  Asp  Phe  Tyr  Leu
          355                           360                365

Phe  Pro  Gly  Asn
          370
```

HUMAN ICE HOMOLOG

FIELD OF THE INVENTION

The present invention is in the field of molecular biology; more particularly, the present invention describes the nucleic acid and amino acid sequences of a novel interleukin-1 converting enzyme homolog derived from activated THP-1 cells.

RELATED AND CO-PENDING APPLICATIONS

This application is related to U.S. application Ser. No. 08/282,991, filed Jul. 28, 1994, which is a continuation-in-part of U.S. application Ser. No. 08/100,523, filed Aug. 3, 1993, and subsequently abandoned.

BACKGROUND OF THE INVENTION

To understand the interleukin 1 converting enzyme (ICE), it is helpful to first examine the role of interleukin-1 (IL-1), its enzymatic substrate. IL-1 facilitates host natural immunity, predominantly those aspects related to the initiation of inflammatory reactions that protect the body against bacterial infection. (Ayala et al. (1994) J. Immunol. 53: 2592–2599). At low concentrations in the bloodstream, IL-1 mediates local inflammation by inducing the synthesis of other cytokines, such as IL-6 and IL-8, and the synthesis of proteins that mediate leukocyte adhesion, and prostaglandin production. (Abbas et al. (1994) Cellular and Molecular Immunology, W.B. Saunders Company). Whereas at intermediate concentrations, IL-1 enters the bloodstream and may induce fever, the synthesis of acute plasma proteins by the liver, and metabolic wasting (cachexia) (Abbas, supra). At even higher concentrations, IL-1 has been implicated in tissue destruction observed in numerous inflammation-related diseases, including rheumatoid arthritis, septic shock, inflammatory bowel disease and insulin-dependent diabetes mellitus. (Li et al. (1995) Cell 80:401–411).

IL-1 activity results from the expression and release of two gene products, IL-1α and IL-1β, predominantly from activated monocytes. (Howard et al. (1991) J. Immunology 147:2964–2969). Both gene products are initially synthesized as inactive precursors of about 31 kDa in monocytes. Pre-IL-1β is cleaved to an active 17 kDa form by the IL-1β-converting enzyme (ICE) before release from activated monocytes. On the other hand, pre-IL-1α is likely cleaved to an active 17 kDa form by a calpain-like IL-1α-converting enzyme prior to release. (Carruth et al. (1991) J. Biol. Chem. 266:12162–12167). Additionally, ICE has been implicated in IL-1α's release from activated monocytes but the mechanism is not understood (Li, supra).

The IL-1β gene product is the predominant form of IL-1 that is present at high concentrations in the bloodstream during inflammatory diseases, such as rheumatoid arthritis, septic shock, inflammatory bowel disease, and insulin-dependent diabetes mellitus (Li, supra). Since the cleavage of pre-IL-1β by ICE is coupled to IL-1β release and to increased IL-1 activity in the bloodstream, ICE activity may be higher in these pathological conditions.

The importance of regulating ICE activity to modulate the IL-1β concentration to affect the host immune response has recently been confirmed: the crmA gene product of cowpox virus prevents the proteolytic activation of IL-1β and inhibits the host inflammatory response. Cowpox virus containing a deleted crmA gene is unable to suppress the inflammatory response, resulting in a reduction of virus-infected cells and less damage to the host. (Miura et al. (1993) Cell 75: 653–660).

ICE is a novel cysteine protease that is known specifically to cleave inactive IL-1β precursor to its active form. (Ayala, supra). This protease recognizes the sequence Asp-X, where X is preferably a small hydrophobic amino acid residue, and cleaves the bond between Asp and X. However, many Asp-X bonds are not recognized by ICE suggesting that flanking sequences or other criteria such as accessibility are also required for recognition and cleavage. In the case of IL-1β, ICE cleaves the precursor to form active IL-1β at two sequence-specific bonds: the bond between residues Asp-27 and Gly-28 and the bond between residues Asp-116 and Ala-117.

ICE itself is synthesized and maintained in cells as an inactive 45 kDa precursor which is processed into the active ICE consisting of 20- and 10-kDa subunits, p20 and p10. (Ayala, supra). Both subunits are derived from the 45 kDa precursor which is cleaved into four different fragments: a 13 kDa precursor domain, the p20, a 2 kDa spacer, and the p10. Since all these polypeptide fragments are flanked by Asp-X residues in the intact 45 kDa precursor it is possible that the ICE precursor is activated autocatalytically. (Ayala, supra).

The three dimensional structure of ICE has been determined from crystallographic studies. (Walker et al. (1994) Cell 78:343–352). First, it is apparent that the active form of ICE is a homodimer of catalytic domains, each of which consists of p20 and p10 subunits. Second, although the active site cysteine residue is located on p20, both p20 and p10 are essential for activity. p20 and p10 structures are intertwined so as to create a unique 6-stranded beta-sheet core flanked on either side by alpha helices. The first 4 beta strands are contributed by p20, while the remaining 2 beta strands are contributed by p10.

The ICE gene from various sources has been sequenced and possesses homology (overall 29% homology) to the product of a gene with a possible role in apoptosis: the Caenorhabditis elegans gene ced-3. (Yuan et al. (1993) Cell 75: 641–652). Additionally, the ICE gene contains a sequence region, spanning residues 166 to 287 of the human ICE gene, which shares a 43% homology with ced-3. It is not known whether ced-3 acts as a cysteine protease but it contains the purported catalytic residues that are located at the ICE active site ($Cys_{285}$ and $His_{237}$). The amino acid pentapeptide Glu-Ala-Cys-Arg-Gly (QACRG), containing the active site cysteine, is the longest peptide conserved among ICE from mice and humans and CED-3 from three different nematodes. Additionally, ced-3 contains the same four residues whose side chains are implicated in binding the aspartate carboxylate group of the substrate at the catalytic site (Arg-179, Gln-283, Ser 347, and Arg-341) (Yuan, supra).

Inhibition with the ICE-specific inhibitor crmA blocks TNF- and FAS-induced apoptosis. Therefore, ICE or a homolog is believed to be involved in TNF- and FAS-induced apoptosis.

Additionally, ICE possesses a degree of homology to a gene product with a possible role in embryogenesis. The mammalian gene Nedd-2/Ich-1 is expressed during embryonic brain development and is down-regulated in the adult brain. (Yuan, supra). Nedd-2, ced-3, and ICE gene products are about 27% homologous with the carboxy terminal of CED-3 and p10 possessing the highest degree of homology to Nedd-2. The Nedd-2 gene product does not contain the same highly conserved cysteine nor the highly conserved QACRG pentapeptide so Nedd-1 probably is not a cysteine protease.

To confirm ICE's role in inflammation-related diseases by controlling the levels of active IL-1β, ICE-deficient knockout mice were created (Li, supra). These genetically-engineered mice were normal physiologically but lacked the ability to process precursor IL-1β to its active form when monocytes were activated with microbial products, such as lipopolysaccharide (LPS). Additionally, the production of IL-1α was decreased, and the level of other cytokines, tumor necrosis factor (TNF) and IL-6, involved in inflammatory responses to microbial products was somewhat reduced. These mice were resistant to the lethal effects of septic shock when exposed to LPS (Li, supra). Therefore, inhibiting ICE activity to lower the concentration of IL-1β in the bloodstream may be a method of treating inflammation-related diseases. ICE also may help identify patients who are susceptible to these diseases.

Since ICE shares sequence homology to ced-3 and overexpression of ICE appears to induce apoptosis, the ICE-deficient mice studies were important because the mice seemed normal in terms of their development. If ICE played a strong role in apoptosis during development, the ICE-deficient mice should have had gross abnormalities in brain, gut, lymphoid and brain tissues (Li, supra). However, ICE may perform functions other than IL-1β precursor cleavage. ICE mRNA has been detected in a greater variety of tissues than IL-1β mRNA has (Miura, supra).

ICE has attracted interest as a target for novel anti-inflammatory drugs, because the cytokine which it activates, IL-1β, is proinflammatory and has been implicated in the pathophysiology of various diseases, including rheumatoid arthritis, septic shock, inflammatory bowel disease and insulin-dependent diabetes mellitus (Dinarello and Wolff (1993) N Engl J Med 328:106–13). The provision of a new ICE gene and polypeptide will further drug research in screening for and designing more effective and more specific inhibitors to this pro-inflammatory substance.

THP-1 Cells

THP-1 is a human leukemic cell line with distinct monocytic characteristics derived from the blood of a 1-year-old boy with acute monocytic leukemia (Tsuchiya S. et al (1980) Int J Cancer 26:171–176). The monocytic nature of THP-1 was established using the following cytological and cytochemical criteria: 1) a-naphthyl butyrate esterase activity which could be inhibited by NaF (sodium fluoride), 2) production of lysozyme, 3) phagocytosis (the engulfing of extracellular materials) of latex particles and sensitized sheep red blood cells, and 4) ability of mitomycin C-treated THP-1 cells to activate T-lymphocytes following concanavalin A treatment. Morphologically, the cytoplasm contained small azurophilic granules, the nucleus was indented and irregularly shaped with deep folds, and the cell membrane had Fc and C3b receptors which probably function in phagocytosis.

Typical monocytes develop from monoblasts through promonocytes in the bone marrow and in their mature form have a half-life of approximately three days. Roughly 75% of the circulating monocyte pool is found along the walls of blood vessels although these cells randomly migrate into tissues and become antigen-presenting or phagocytic. Antigen-presenting monocytes include interdigitating reticular and follicular dendritic cells of the lymph nodes and skin. Phagocytic monocytes are prominent as Kupffer cells of the liver and in the lung alveoli and bone marrow.

Whereas precursor monocytes are rich in azurophilic, peroxidase-containing cytoplasmic granules, macrophages have more numerous cell surface receptors by which they monitor their environment. These include receptors for immunoglobulin, complement, growth factors, lipoproteins, peptides and polysaccharides. Binding of ligands to these receptors triggers macrophage proliferation, chemotaxis, secretion and phagocytosis.

Many human myeloid and myelomonocytic cell lines retain some ability to differentiate into more mature phenotypes in response to various internal stimuli including growth factors, lymphokines, cytokines, vitamin D derivatives, and tumor promoters and external agents such as trauma, smoking, UV irradiation, asbestos exposure, and steroids. THP-1 cells treated with the tumor promoter 12-O-tetradecanoyl-phorbol-13 acetate (TPA) are induced to stop proliferating and differentiate into macrophage-like cells which mimic native monocyte-derived macrophages both morphologically and physiologically.

These monocyte/macrophage-like cells exhibit changes in gene expression such as the coinduction of C-fos and c-jun and the down-regulation of c-myb (Auwerx J. (1991) Experientia 47:22–31), increase in density of the complement C3b receptor, and decrease in both FcR and the adhesion molecule, CD4. In addition, THP-1 cells produce lipoprotein lipase and apolipoprotein E associated with atherosclerotic lesions, secrete several proinflammatory cytokines, including IL-1β and TNF (Cochran FR and Finch-Arietta MB (1989) Agents and Actions 27:271–273), and may elaborate powerful oxidants and tissue destroying proteases, such as the IL-1 converting enzyme.

SUMMARY OF THE INVENTION

The subject invention provides a unique nucleotide sequence SEQ ID NO: 5 which encodes a novel human ICE homolog SEQ ID NO: 6. The new gene, also known as icey, which was identified within Incyte Clone 14775, encodes ICEY polypeptide and represents a new human cysteine protease. This ICE homolog was found in a library of activated monocytic cells, namely,phorbol- and endotoxin-treated THP-1 cells.

The invention also comprises diagnostic tests for physiologic or pathologic activity of activated monocytes or macrophages which include the steps of testing a sample or an extract thereof with ICE homolog-encoding cDNA, fragments or oligomers thereof. Further aspects of the invention include the antisense of icey; cloning or expression vectors containing icey; host cells or organisms transformed with expression vectors containing icey; a method for the production and recovery of purified ICEY polypeptide from host cells; purified ICEY polypeptide; antibodies and inhibitors to ICEY, and pharmacological compounds using ICEY antibodies.

DESCRIPTION OF THE FIGURES

FIGS. 1A–1C display the nucleotide sequence (SEQ ID NO: 5) for ice homolog and the predicted amino acid sequence of ICE homolog (SEQ ID NO: 6).

FIGS. 2A and 2B show the amino acid alignment of the novel ICE homolog with the reference human ICE. Alignments shown were produced using the multisequence alignment program of DNASTAR software (DNASTAR Inc, Madison Wis.).

DETAILED DESCRIPTION OF THE INVENTION

Definitions

Figure 3:
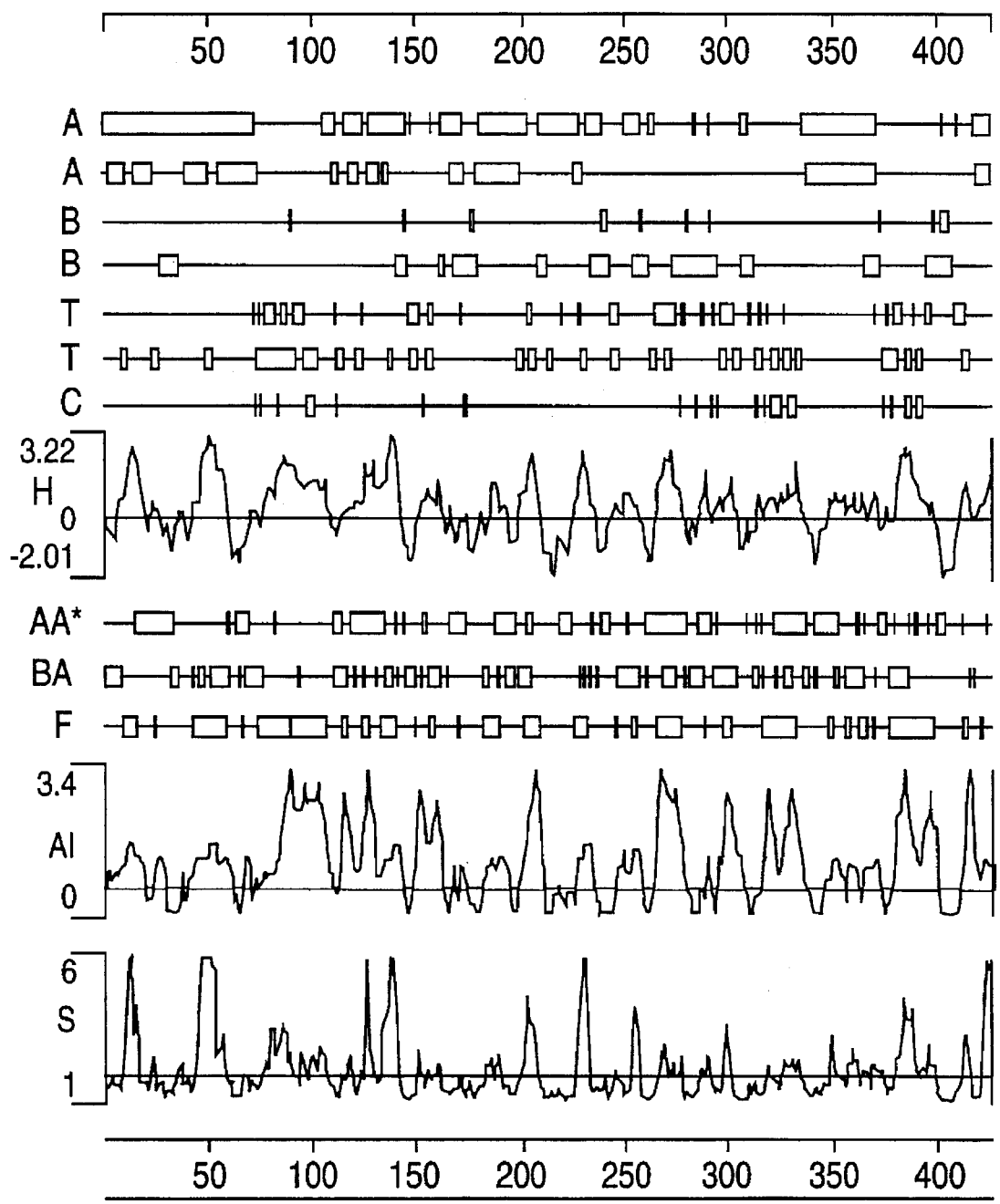
FIG. 3 displays an analysis of ICE homolog alpha regions (A), beta regions (B), turn regions (T), coil regions (C), hydrophilicity plot (H), alpha amphipathic regions (AA), beta amphipathic regions (BA), antigenic index (AI) and surface probability plot (S) based on the predicted acid amino sequence and composition.

As used herein, ICE homolog (ICEY) refers to a homolog of human ICE, naturally occurring ICEY, or active fragments thereof, which are encoded by mRNAs transcribed from the cDNA of FIGS. 1A and 1B.

"Active" refers to those forms of ICEY which retain biologic and/or immunologic activities of any naturally occurring ICEY.

"Naturally occurring ICEY" refers to ICEY produced by human cells that have not been genetically engineered and specifically contemplates various ICEYs arising from post-translational modifications of the polypeptide including but not limited to acetylation, carboxylation, glycosylation, phosphorylation, lipidation and acylation.

"Derivative" refers to polypeptides derived from naturally occurring ICEY by chemical modifications such as ubiquitination, labeling (e.g., with radionuclides, various enzymes, etc.), pegylation (derivatization with polyethylene glycol), or by insertion (or substitution by chemical synthesis) of amino acids (aa) such as ornithine, which do not normally occur in human proteins.

"Recombinant variant" refers to any polypeptide differing from naturally occurring ICEY by amino acid insertions, deletions, and substitutions, created using recombinant DNA techniques. Guidance in determining which amino acid residues may be replaced, added or deleted without abolishing activities of interest, such as cell adhesion and chemotaxis, may be found by comparing the sequence of the particular ICEY with that of homologous molecules and minimizing the number of amino acid sequence changes made in regions of high homology.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, i.e., conservative aa replacements. "Insertions" or "deletions" are typically in the range of about 1 to 5 amino acid. The variation allowed may be experimentally determined by systematically making insertions, deletions, or substitutions of amino acid in an ICEY molecule using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acid, often at least about 7 amino acid, typically at least about 9 to 13 amino acid, and, in various embodiments, at least about 17 or more amino acid. To be active, any ICEY polypeptide must have sufficient length to display biologic and/or immunologic activity on their own or when conjugated to a carrier protein such as keyhole limpet hemocyanin.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules. One or both oligonucleotide probes will comprise sequence that is identical or complementary to a portion of icey where there is little or no identity or complementarity with any known or prior art molecule. The oligonucleotide probes will generally comprise between about 10 nucleotides and 50 nucleotides, and preferably between about 15 nucleotides and about 30 nucleotides.

"Activated monocytes" as used herein refers to the activated, mature monocytes or macrophages found in immunologically active tissues.

"Monocyte/macrophage disorders" include but are not limited to inflammatory bowel disease, insulin-dependent diabetes mellitus, rheumatoid arthritis, and sepsis.

"Animal" as used herein may be defined to include human, domestic or agricultural (cats, dogs, cows, sheep, etc) or test species (mouse, rat, rabbit, etc).

The present invention includes purified ICEY polypeptides from natural or recombinant sources, cells transformed with recombinant nucleic acid molecules encoding ICEY. Various methods for the isolation of the ICEY polypeptides may be accomplished by procedures well known in the art. For example, such polypeptides may be purified by immunoaffinity chromatography by employing the antibodies provided by the present invention. Various other methods of protein purification well known in the art include those described in Deutscher M. (1990) Methods in Enzymology, Vol 182, Academic Press, San Diego Calif.; and Scopes R (1982) Protein Purification: Principles and Practice. Springer-Verlag, New York City, both incorporated herein by reference.

"Recombinant" may also refer to a polynucleotide which encodes ICEY and is prepared using recombinant DNA techniques. The DNAs which encode ICEY may also include allelic or recombinant variants and mutants thereof.

"Nucleic acid probes" are prepared based on the cDNA sequences which encode ICEY provided by the present invention. Nucleic acid probes comprise portions of the sequence having fewer nucleotides than about 6 kb, usually fewer than about 1 kb. After appropriate testing to eliminate false positives, these probes may be used to determine whether mRNAs encoding ICEY are present in a cell or tissue and to isolate similar nucleic acid sequences from chromosomal DNA extracted from such cells or tissues as described by Walsh P. S. et al (1992, PCR Methods Appl 1:241–250).

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J. et al (1989) Molecular Cloning: A Laboratory Manual, Cold Spring Harbor Laboratory, Cold Spring Harbor N.Y.; or Ausubel F. M. et al (1989) Current Protocols in Molecular Biology, John Wiley & Sons, New York City, both incorporated herein by reference.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, including but not limited to ligand-binding affinities, interchain affinities, polypeptide degradation and turnover rate. One example involves inserting a stop codon into the nucleotide sequence to limit the size of ICEY so as to provide a binding, non-activating ligand of smaller molecular mass which would serve to block the activity of the natural ICEY.

"ICE inhibitors", or ICE-like molecules that bind IL-1 but do not activate it, can be synthesized recombinantly by substituting the cysteine for other natural (such as alanine) or synthetic amino acid in the active pentapeptide site, such that the substituted molecule has the aforesaid attributes. Alternately, the cysteine can be chemically modified by methods routine in the art, so as to inhibit activation.

ICE homologs with modified specificity can be readily synthesized by substituting the non-cysteine residues of the conserved pentapeptide. Such recombinant mutants are well known in the art; substitution of the four amino acid with other natural and synthetic amino acid is readily performed. Activity is tested by the methods disclosed in the cited references.

DETAILED DESCRIPTION OF THE INVENTION

The present invention provides a nucleotide sequence found within Incyte clone 14775 uniquely identifying a new, human ICE homolog (ICEY) of the cysteine protease family which is expressed in treated THP-1 cells. Because ICEY is specifically expressed in activated monocytes, the nucleic acids (icey), polypeptides (ICEY) and antibodies to ICEY are useful in diagnostic assays based on production of ICEY in cases of inflammation or inflammatory disease processes. Excessive expression of ICEY may lead to tissue damage or destruction. Therefore, a diagnostic test for ICEY can accelerate diagnosis and proper treatment of activated monocyte disorders including inflammatory bowel disease, insulin-dependent diabetes mellitus, rheumatoid arthritis, septic shock and similar pathologic problems.

The nucleotide sequences encoding ICEY (or their complement) have numerous applications in techniques known to those skilled in the art of molecular biology. These techniques include use as hybridization probes, use in the construction of oligomers for PCR, use for chromosome and gene mapping, use in the recombinant production of ICEY, and use in generation of anti-sense DNA or RNA, their chemical analogs and the like. Uses of nucleotides encoding ICEY disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of ICEY-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring icey, and all such variations are to be considered as being specifically disclosed.

Although the nucleotide sequences which encode ICEY and/or its variants are preferably capable of hybridizing to the nucleotide sequence of the naturally occurring icey under stringent conditions, it may be advantageous to produce nucleotide sequences encoding ICEY or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding ICEY and/or its derivatives without altering the encoded amino acid sequence include the production of RNA transcripts having more desirable properties, such as a greater half-life, than transcripts produced from the naturally occurring sequence.

Nucleotide sequences encoding ICEY may be joined to a variety of other nucleotide sequences by means of well established recombinant DNA techniques (cf Sambrook J. et al., supra). Useful nucleotide sequences for joining to icey include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for icey-specific nucleic acid hybridization probes capable of hybridizing with naturally occurring nucleotide sequences encoding ICEY. Such probes may also be used for the detection of similar ICEY encoding sequences and should preferably contain at least 50% of the nucleotides from the conserved region or active site. The hybridization probes of the subject invention may be derived from the nucleotide sequences of the FIGS. 1A and 1B or from genomic sequences including promoters, enhancer elements and/or possible introns of the respective naturally occurring iceys. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

PCR as described U.S. Pat. Nos. 4,683,195; 4,800,195; and 4,965,188 provides additional uses for oligonucleotides based upon the nucleotide sequence which encodes ICEY. Such probes used in PCR may be of recombinant origin, may be chemically synthesized, or a mixture of both and comprise a discrete nucleotide sequence for diagnostic use or a degenerate pool of possible sequences for identification of closely related genomic sequences.

Other means of producing specific hybridization probes for icey DNAs include the cloning of nucleic acid sequences encoding ICEY or ICEY derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding ICEY and their derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the icey sequences or any portion thereof.

The nucleotide sequence can be used in an assay to detect inflammation or disease associated with abnormal levels of expression of ICEY. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantified and compared with a standard. If the amount of dye is significantly elevated, the nucleotide sequence has hybridized with the sample, and the assay indicates the presence of inflammation and/or disease.

The nucleotide sequence for icey can be used to construct hybridization probes for mapping that gene. The nucleotide sequence provided herein may be mapped to a particular chromosome or to specific regions of that chromosome using well known genetic and/or chromosomal mapping techniques. These techniques include in situ hybridization, linkage analysis against known chromosomal markers, hybridization screening with libraries, flow-sorted chromosomal preparations, or artificial chromosome constructions YAC, P1 or BAC constructions. The technique of fluorescent in situ hybridization of chromosome spreads has been described, among other places, in Verma et al (1988) Human Chromosomes: A Manual of Basic Techniques, Pergamon Press, New York City.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of icey on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

Nucleotide sequences encoding ICEY may be used to produce purified ICEY using well known methods of recombinant DNA technology. Among the many publications that teach methods for the expression of genes after they have been isolated is Goeddel (1990) Gene Expression Technology, Methods and Enzymology, Vol 185, Academic Press, San Diego Calif. ICEY may be expressed in a variety of host cells, either prokaryotic or eukaryotic. Host cells may be from the same species in which icey nucleotide sequences are endogenous or from a different species. Advantages of producing ICEY by recombinant DNA technology include obtaining adequate amounts of the protein for purification and the availability of simplified purification procedures.

Cells transformed with DNA encoding ICEY may be cultured under conditions suitable for the expression of ICEY and recovery of the protein from the cell culture. ICEY produced by a recombinant cell may be secreted or may be contained intracellularly, depending on the ICEY sequence and the genetic construction used. In general, it is more convenient to prepare recombinant proteins in secreted form. Purification steps vary with the production process and the particular protein produced.

In addition to recombinant production, fragments of ICEY may be produced by direct peptide synthesis using solid-phase techniques (cf Stewart et al (1969) Solid-Phase Peptide Synthesis, WH Freeman Co, San Francisco Calif.; Merrifield J. (1963) J Am Chem Soc 85:2149–2154. In vitro protein synthesis may be performed using manual techniques or by automation. Automated synthesis may be achieved, for example, using Applied Biosystems 431A Peptide Synthesizer (Foster City, Calif.) in accordance with the instructions provided by the manufacturer. Various fragments of ICEY may be chemically synthesized separately and combined using chemical methods to produce the full length molecule.

ICEY for antibody induction does not require biological activity; however, the protein must be immunogenic. Peptides used to induce specific antibodies may have an amino acid sequence consisting of at least five amino acid, preferably at least 10 amino acid. They should mimic a portion of the amino acid sequence of the protein and may contain the entire amino acid sequence of a small naturally occurring molecule such as ICEY. Short stretches of ICEY amino acid may be fused with those of another protein such as keyhole limpet hemocyanin and the chimeric molecule used for antibody production.

Antibodies specific for ICEY may be produced by inoculation of an appropriate animal with the polypeptide or an antigenic fragment. An antibody is specific for ICEY if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R. et al (1989) PNAS 86:3833–3837; Huse W. D. et al (1989) Science 256:1275–1281) or the in vitro stimulation of lymphocyte populations. Current technology (Winter G. and Milstein C. (1991) Nature 349:293–299) provides for a number of highly specific binding reagents based on the principles of antibody formation. These techniques may be adapted to produce molecules specifically binding ICEYs.

An additional embodiment of the subject invention is the use of ICEY specific antibodies, inhibitors, receptors or their analogs as bioactive agents to treat activated monocyte disorders, such as inflammatory bowel disease, insulin-dependent diabetes mellitus, rheumatoid arthritis, septic shock and similar pathologic problems.

Bioactive compositions comprising agonists, antagonists, receptors or inhibitors of ICEY may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving ICEY production and function.

The examples below are provided to illustrate the subject invention. These examples are provided by way of illustration and are not included for the purpose of limiting the invention.

EXAMPLES

I Isolation of mRNA and Construction of cDNA Libraries

The icey sequence was identified among the unique sequences 14775 (SEQ ID NO: 1) and 157811 (SEQ ID NO: 2) obtained from human activated THP-1 libraries. THP-1 is a human leukemic cell line derived from the blood of a 1-year-old boy with acute monocytic leukemia. Cells used for the activated (or PMA+LPS) library were cultured for 48 hr with 100 nm PMA in DMSO and for 4 hr with 1 μg/ml LPS. The activated THP-1 library was custom constructed by Stratagene (Stratagene, 11099 M. Torrey Pines Rd., La Jolla, Calif. 92037) essentially as described below.

Stratagene prepared the cDNA library using oligo d(T) priming. Synthetic adapter oligonucleotides were ligated onto the cDNA molecules enabling them to be inserted into the Uni-ZAP™ vector system (Stratagene). This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into E. Coli host strain XL1-Blue® (Stratagene). The high transformation efficiency of this bacterial strain increases the probability that the cDNA library will contain rare, under-represented clones. Alternative unidirectional vectors might include, but are not limited to, pcDNAI (Invitrogen, San Diego Calif.) and pSHIox-1 (Novagen, Madison Wis.).

II Isolation of cDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the pBluescript plasmid and the cDNA insert. The phagemid DNA was released from the cells and purified, then used to re-infect fresh bacterial host cells (SOLR, Stratagene Inc), where the double-stranded phagemid DNA was produced. Because the phagemid carries the gene for β-lactamase, the newly transformed bacteria were selected on medium containing ampicillin.

Phagemid DNA was purified using the QIAWELL-8 Plasmid Purification System from QIAGEN® DNA Purification System. This technique provides a rapid and reliable high-throughput method for lysing the bacterial cells and isolating highly purified phagemid DNA. The DNA eluted from the purification resin was suitable for DNA sequencing and other analytical manipulations.

III Sequencing of cDNA Clones

The cDNA inserts from random isolates of the THP-1 library were sequenced in part. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 377 or 373 DNA sequencer).

IV Homology Searching of cDNA Clones and Deduced Proteins

Each sequence so obtained was compared to sequences in GenBank using a search algorithm developed by Applied Biosystems Inc. and incorporated into the INHERIT™ 670 Sequence Analysis System. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments of the protein sequence were used to display the results of the homology search. This method did not immediately identify an ICE homolog. Subsequently, the human ICE sequence was obtained from GenBank and compared with the sequences in the LIFESEQ™ database (Incyte Pharmaceuticals, Inc.). Incyte clones 14775 and 157811 were determined to have homology to the Genbank sequence. The presence of icey in the activated THP-1 library, which represents activated macrophages, is consistent with its expression in tissues with active immunological defenses, particularly inflamed and diseased tissues, including those previously defined relative to activated monocyte disorders.

Peptide and protein sequence homologies were ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

The nucleotide and amino acid sequences for the entire coding region of the human ICE homolog, ICEY, claimed in this invention are shown in FIGS. 1A and 1B (SEQ ID NO: 5 and SEQ ID NO: 6).

V Identification and Full Length Sequencing of the Genes

Figure 4:
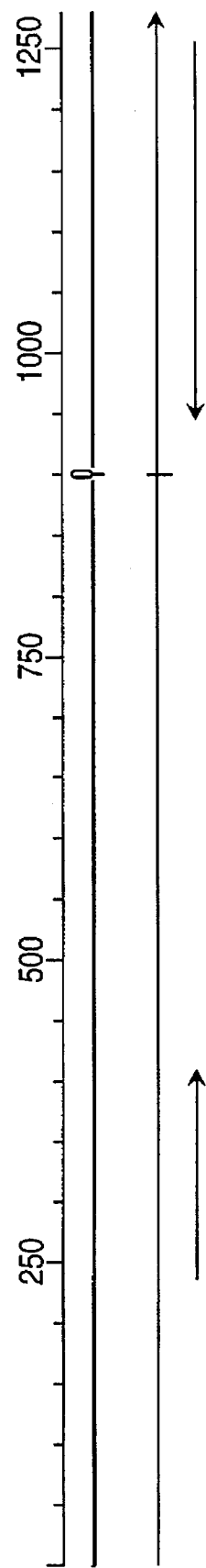
FIG. 4 displays the alignment of the partial cDNA sequences with the complete icey gene.

Incyte clones numbered 14775 and 157811 (SEQ ID NO: 1 and SEQ ID NO: 2, respectively) were resequenced with M13 and M13 reverse primers to obtain additional 3' and 5' nucleotide sequence. The additional sequences did not overlap, indicating that the coding region was incomplete. Because only clone 14775 appeared to have the Complete coding region, that clone alone was primed with newly designed oligos (SEQ ID NO: 3 and SEQ ID NO: 4) to obtain internal sequence to finish the nucleotide sequence of the gene. The additional sequence which had been obtained from clone 157811 was used to confirm and edit the sequences from clone 14775. The confirmed icey sequence was homologous to but clearly different from any known ICE molecule. The complete nucleotide sequence for icey was translated, and the in-frame translation is shown in FIGS. 1A and 1B. When all three possible predicted translations of the sequence were searched against protein databases such as SwissProt and PIR, no exact matches were found to any of the possible translations of icey. FIGS. 2A and 2B show the comparison of the ICEY amino acid sequence with human ICE. Amino acids in agreement are highlighted in black. The expected structure (alpha, beta, and flexible regions), as well as hydrophilicity and antigenicity plots for ICEY are shown as FIG. 3. FIG. 4 shows the alignments of the completed gene sequence (top line) (SEQ ID NO: 5) with the partial cDNA sequences of clones numbered 14775 and 157811 (SEQ ID NO: 1 and SEQ ID NO: 2, respectively). The sequence alignment of SEQ ID NO: 1 is shown on the left and that of SEQ ID NO: 2 on the right.

VI Antisense analysis

Knowledge of the correct, complete cDNA sequence of the new icey gene will enable its use in antisense technology in the investigation of gene function. Oligonucleotides, genomic or cDNA fragments comprising the antisense strand of icey can be used either in vitro or in vivo to inhibit expression of the protein. Such technology is now well known in the art, and probes can be designed at various locations along the nucleotide sequence. By treatment of cells or whole test animals with such antisense sequences, the gene of interest can effectively be turned off. Frequently, the function of the gene can be ascertained by observing behavior at the cellular, tissue or organismal level (e.g. lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of ICEY

Expression of icey may be accomplished by subcloning the cDNAs into appropriate expression vectors and transfecting the vectors into appropriate expression hosts. In this particular case, the cloning vector previously used for the generation of the tissue library also provide for direct expression of the included icey sequence in *E. Coli*. Upstream of the cloning site, this vector contains a promoter for β-galactosidase, followed by sequence containing the amino terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The icey cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as Saccharomyces cerevisiae, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts; or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced ICEY can be recovered from the conditioned medium and analyzed using chromatographic methods known in the art. Because expression of the ICEY protein may be lethal to certain cell types, care should be given to the selection of a suitable host species. Alternately, the protein can be expressed in the inactive form, such as in inclusion bodies. The inclusion bodies can be separated from the cells, the protein solubilized and refolded into active form.

VIII Isolation of Recombinant ICEY

ICEY may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen, San Diego Calif.) between the purification domain and the icey sequence may be useful to facilitate expression of ICEY.

IX Production of ICEY Specific Antibodies

Two approaches are utilized to raise antibodies to ICEY, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of ICEY, as deduced from translation of the cDNA, is analyzed to determine regions of high immunogenicity. Oligopeptides comprising appropriate hydrophilic regions, as shown in FIG. 3, are synthesized and used in suitable immunization protocols to raise antibodies. Analysis to select appropriate epitopes is described by Ausubel F. M. et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; cf. Ausubel F. M. et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled ICEY to identify those fusions producing the monoclonal antibody with the desired specificity. In a typical protocol, wells of plates (FAST; Becton-Dickinson, Palo Alto, Calif.) are coated with affinity purified, specific rabbit-anti-mouse antibodies (or suitable anti-species Ig) at 10 mg/ml. The coated wells are blocked with 1% BSA, washed and exposed to supernatants from hybridomas. After incubation the wells are exposed to labeled ICEY, 1 mg/ml. Clones producing antibodies will bind a quantity of labeled ICEY which is detectable above background. Such clones are expanded and subjected to 2 cycles of cloning at limiting dilution (1 cell/3 wells). Cloned hybridomas are injected into pristane mice to produce ascites, and monoclonal antibody is purified from mouse ascitic fluid by affinity chromatography on Protein A. Monoclonal antibodies with affinities of at least $10^{8M-1}$, preferably $10^9$ to $10^{10}$ or stronger, will typically be made by standard procedures as described in Harlow and Lane (1988) Antibodies: A Laboratory Manual. Cold Spring Harbor Laboratory, Cold Spring Harbor N.Y.; and in Goding (1986) Monoclonal Antibodies: Principles and Practice, Academic Press, New York City, both incorporated herein by reference.

X Diagnostic Test Using ICEY Specific Antibodies

Particular ICEY antibodies are useful for the diagnosis of prepathologic conditions, and chronic or acute diseases which are characterized by differences in the amount or distribution of ICEY. To date, ICEY has been found only in the activated THP-1 library and is thus associated with abnormalities or pathologies which activate monocytes.

Diagnostic tests for ICEY include methods utilizing the antibody and a label to detect ICEY in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound ICEY, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on ICEY is preferred, but a competitive binding assay may be employed. These assays are described, among other places, in Maddox, D. E. et al (1983, J Exp Med 158:1211).

XI Purification of Native ICEY Using Specific Antibodies

Native or recombinant ICEY can be purified by immunoaffinity chromatography using antibodies specific for ICEY. In general, an immunoaffinity column is constructed by covalently coupling the anti-ICEY antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of ICEY by preparing a fraction from cells containing ICEY in a soluble form. This preparation is derived by solubilization of the whole cell or of a subcellular fraction obtained via differential centrifugation by the addition of detergent or by other methods well known in the art. Alternatively, soluble ICEY containing a signal sequence may be secreted in useful quantity into the medium in which the cells are grown.

A soluble ICEY-containing preparation is passed over the immunoaffinity column, and the column is washed under conditions that allow the preferential absorbance of ICEY (eg, high ionic strength buffers in the presence of detergent). Then, the column is eluted under conditions that disrupt antibody/ICEY binding (e.g., a buffer of pH 2–3 or a high concentration of a chaotrope such as urea or thiocyanate ion), and ICEY is collected.

XII ICEY Activity

The activity of purified or expressed ICEY may be tested by the methods taught in the ICE references cited above. One such method calls for stimulating macrophages with LPS to induce the expression of pre-IL-1β and then treating with ATP and ICEY. Mature IL-1β levels in the medium then can be measured by enzyme-linked immunosorbent assay (ELISA), as described in Li et al. (1995) Cell 80:401–411.

XIII Drug Screening

This invention is particularly useful for screening compounds by using ICEY polypeptide or binding fragments thereof in any of a variety of drug screening techniques. The ICEY polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between ICEY and the agent being tested. Alternatively, one can examine the diminution in complex formation between ICEY and its target cell, the monocyte or macrophage, caused by the agent being tested.

Thus, the present invention provides methods of screening for drugs, natural inhibitors or any other agents which can affect inflammation and disease. These methods comprise contacting such an agent with a ICEY polypeptide or fragment thereof and assaying 1) for the presence of a complex between the agent and the ICEY polypeptide or fragment, or 2) for the presence of a complex between the ICEY polypeptide or fragment and the cell, by methods well known in the art. In such competitive binding assays, the ICEY polypeptide or fragment is typically labeled. After suitable incubation, free ICEY polypeptide or fragment is separated from that present in bound form, and the amount of free or uncomplexed label is a measure of the ability of the particular agent to bind to ICEY or to interfere with the ICEY and agent complex.

Another technique for drug screening provides high throughput screening for compounds having suitable binding affinity to the ICEY polypeptide and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with ICEY polypeptide and washed. Bound ICEY polypeptide is then detected by methods well known in the art. Purified ICEY can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding ICEY specifically compete with a test compound for binding to ICEY polypeptides or fragments thereof. In this manner, the antibodies can be used to detect the presence of any peptide which shares one or more antigenic determinants with ICEY.

XIV Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf Hodgson J. (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. However, the crystal structure of one ICE protein is known (Walker, 1994, supra) and can be used as a starting point. In both cases, relevant structural information is used to design analogous ICEY-like molecules or to identify efficient inhibitors. Useful examples of rational drug design include molecules which have different specificity or improved activity or stability as shown by Braxton S. and Wells J. A. (1992 Biochemistry 31:7796–7801) or which act as inhibitors, agonists, or antagonists of native peptides as shown by Athauda S. B. et al (1993 J Biochem 113:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the ICEY amino acid sequence provided herein will provide guidance to those employing computer modeling techniques in place of or in addition to x-ray crystallography.

XV Use and Administration of ICEY

Antibodies, inhibitors, or antagonists of ICEY (or other treatments for excessive ICEY production, hereinafter abbreviated TEC), can provide different effects when administered therapeutically. TECs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of TEC include solubility of the molecule, half-life and immunogenicity; these and other characteristics may aid in defining an effective carrier. Native human proteins are preferred as TECs, but organic or synthetic molecules resulting from drug screens may be equally effective in particular situations.

TECs may be delivered by known routes of administration including but not limited to topical creams and gels; transmucosal spray and aerosol, transdermal patch and bandage; injectable, intravenous and lavage formulations; and orally administered liquids and pills, particularly formulated to resist stomach acid and enzymes. The particular formulation, exact dosage, and route of administration will be determined by the attending physician and will vary according to each specific situation.

Such determinations are made by considering multiple variables such as the condition to be treated, the TEC to be administered, and the pharmacokinetic profile of the particular TEC. Additional factors which may be taken into account include disease state (e.g. severity) of the patient, age, weight, gender, diet, time of administration, drug combination, reaction sensitivities, and tolerance/response to therapy. Long-acting TEC formulations might be administered only once per day, or even less often: every 3 to 4 days, every week, or every two weeks depending on half-life and clearance rate of the particular TEC.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different TECs and that administration targeting the eosinophil may necessitate delivery in a manner different from that to another organ or tissue.

It is contemplated that conditions or diseases which activate monocytes, macrophages and possibly other leukocytes may precipitate damage that is treatable with TECs. Activated monocyte disorders may be specifically diagnosed by the tests discussed above, and such testing should be performed in suspected cases of inflammatory bowel disease, insulin-dependent diabetes mellitus, rheumatoid arthritis, sepsis and similar physiologic/pathologic problems.

All publications and patents mentioned in the above specification are herein incorporated by reference. The foregoing written specification is considered to be sufficient to enable one skilled in the art to practice the invention. Indeed, various modifications of the above described modes for carrying out the invention which are readily apparent to those skilled in the field of molecular biology or related fields are intended to be within the scope of the following claims.

We claim:

1. An isolated and purified polynucleotide consisting of a polynucleotide sequence encoding the polypeptide having the sequence shown in SEQ ID NO:6.

2. An isolated and purified polynucleotide wherein the polynucleotide sequence consists of SEQ ID NO:5, or its complementary sequence.

3. An expression vector comprising the polynucleotide of claim 2.

4. A host cell comprising the expression vector of claim 3.

5. A method for producing human interleukin-1 converting enzyme (ICEY), said method comprising the steps of:
   a) culturing the host cells of claim 4 to allow expression of ICEY, and
   b) recovering ICEY from the cell culture.

6. A purified human interleukin-1 converting enzyme (ICEY) having the amino, acid sequence shown in SEQ ID NO:6.

7. A method of screening a plurality of compounds for binding affinity with the human interleukin-1 converting enzyme (ICEY) of claim 6, said method comprising the steps of:
   a) providing a plurality of compounds;
   b) combining the compounds with ICEY for a time sufficient for the compound to bind ICEY; and
   c) detecting and recovering the compound which binds ICEY.

8. A method for the detection of polynucleotides encoding human interleukin-1 converting enzyme (ICEY) in a biological sample wherein the presence of ICEY is associated with a disease comprising the steps of:
   a) hybridizing a polynucleotide having the sequence shown in SEQ ID NO:5 to nucleic acid material of a biological sample, thereby forming a hybridization complex, and
   b) detecting said hybridization complex, wherein the presence of said complex correlates with the presence of a polynucleotide encoding ICEY in said biological sample.

9. The method of claim 8 wherein the disease is selected from the group consisting of rheumatoid arthritis, inflammatory bowel disease, insulin-dependent diabetes melitus and septic shock.

10. A method for the detection of human interleukin-1 converting enzyme (ICEY) in a biological sample, wherein the presence of ICEY is associated with a disease state, comprising the steps of:
   a) combining an anti-ICEY antibody with a biological sample under conditions suitable for the formation of an antibody-antigen complex,
   b) detecting said antibody-antigen complex, wherein the presence of said complex correlates with the presence of ICEY in said biological sample, and
   c) comparing the levels of ICEY in said biological sample with a standard thereby determining the presence of abnormal levels of ICEY.

* * * * *